(12) United States Patent
Velip et al.

(10) Patent No.: US 10,292,947 B2
(45) Date of Patent: May 21, 2019

(54) PHARMACEUTICAL COMPOSITIONS FOR N-PROPARGYLAMINE DERIVATIVE

(71) Applicant: Dr. Reddy's Laboratories Ltd., Hyderabad, Telangana (IN)

(72) Inventors: Chandrakant Bamtu Velip, Goa (IN); Anup Avijit Choudhury, Odisha (IN); Girish Karanth, Telangana (IN); Rajeev Singh Raghuvanshi, Gurgaon (IN)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 85 days.

(21) Appl. No.: 15/470,514

(22) Filed: Mar. 27, 2017

(65) Prior Publication Data
US 2017/0273918 A1    Sep. 28, 2017

(30) Foreign Application Priority Data

Mar. 26, 2016   (IN) .............................. 201641006786

(51) Int. Cl.
| | | |
|---|---|---|
| *A61K 31/135* | (2006.01) | |
| *A61K 9/20* | (2006.01) | |
| *A61K 9/00* | (2006.01) | |
| *A61K 47/26* | (2006.01) | |
| *A61K 47/32* | (2006.01) | |
| *A61K 31/00* | (2006.01) | |

(52) U.S. Cl.
CPC .......... *A61K 31/135* (2013.01); *A61K 9/0056* (2013.01); *A61K 9/2013* (2013.01); *A61K 9/2018* (2013.01); *A61K 9/2027* (2013.01); *A61K 31/00* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | |
|---|---|---|
| 2008/0107729 A1 | 5/2008 | Amin et al. |
| 2012/0122993 A1 | 5/2012 | Talasila et al. |
| 2015/0031774 A1 | 1/2015 | Patashnik et al. |

FOREIGN PATENT DOCUMENTS

| | | | |
|---|---|---|---|
| CN | 1911211 A | * | 2/2007 |
| CN | 1911211 A |   | 2/2007 |
| WO | WO198704342 | * | 6/1987 |
| WO | 2010/111264 A2 |   | 9/2010 |
| WO | WO2011010324 | * | 1/2011 |

OTHER PUBLICATIONS

Guo, J. in Drug Development & Delivery 3(6), 1-3 (2003) (Year: 2003).*
European Patent Office, International Search Report and Written Opinion issued in corresponding Application No. PCT/IB2017/000402, dated Jul. 3, 2017.

* cited by examiner

*Primary Examiner* — Dennis Heyer
(74) *Attorney, Agent, or Firm* — Stites & Harbison, PLLC; Mandy Wilson Decker

(57) ABSTRACT

The present application relates to a method of treating Parkinson's disease by administering a mouth-dissolving composition of N-propargylamine derivative, such as rasagiline or a pharmaceutically-acceptable salt thereof.

18 Claims, 3 Drawing Sheets

PHARMACEUTICAL COMPOSITIONS FOR N-PROPARGYLAMINE DERIVATIVE

RELATED APPLICATIONS

This application claims priority from Indian Provisional Application No. IN 201641006786, dated Mar. 26, 2016, the entire disclosure of which is incorporated herein by this reference.

TECHNICAL FIELD

The present application relates to a method and composition for treating Parkinson's disease. The method involves orally-administering a mouth-dissolving composition of an N-propargylamine derivative to a subject in need thereof. The method and composition provide ease of administration and rapid absorption of the N-propargylamine derivative for improved patient compliance.

BACKGROUND

Parkinson's disease (PD) is a progressive disorder, which can begin with mild limb stiffness and infrequent tremors, which progress over a period of ten or more years to frequent tremors and memory impairment, and ultimately to uncontrollable tremors and dementia. Parkinson's disease affects about 10 million people world-wide. The disease produces a slowly-increasing disability in purposeful movement. A perceived pathophysiological cause of Parkinson's disease is progressive destruction of dopamine-producing cells in the basal ganglia, which comprise the pars compacta of the substantia nigra, a basal nuclei located in the brain stem. Loss of dopamineric neurons results in a relative excess of acetylcholine.

The understanding that parkinsonism is a syndrome of dopamine deficiency and the discovery of levodopa as an important drug for the treatment of the disease were the logical culmination of a series of related basic and clinical observations, which serves as the rationale for drug treatment. Appropriate management of a patient with PD is possible in the first 5-7 years of treatment, after which time a series of often debilitating complications, together referred to as late motor fluctuations (LMF) occur. Thus, effective treatment of Parkinson's disease can be very difficult considering the complexity of the disease etiology and progression.

Current treatments for PD include drugs, ablative surgical intervention, and/or neural stimulation. Drug treatments or therapies may include levodopa; carbidopa; benserazide; entacapone; dopamine agonists like rotigotine, pramipexole, ropinirole, apomorphine; monoamine oxidase-B (MAO-B) inhibitors like selegiline, rasagiline, safinamide, tranylcypromine; COMT inhibitors like entacapone, tolcapone; and glutamate antagonists like amantadine. Unfortunately, such drug therapies frequently become less effective or ineffective over the time. A PD patient may require multiple drugs in combination to extend the time period of efficacy of drug therapies.

It is believed that treatment with levodopa, the most effective antiparkinson drug, may facilitate or even promote the appearance of LMF. Dopamine agonists are employed as a treatment alternative, but they do not offer the same degree of symptomatic relief to patients as levodopa does. Drug treatments additionally have a significant likelihood of inducing undesirable physical side effects. For example, motor function complications, such as uncontrollable involuntary movements (dyskinesias), are a particularly common side effect.

Systemically-administered anticholinergic drugs (such as benzhexol and orphenedrine) have also been used to treat Parkinson's disease and act by reducing the amount of acetylcholine produced in the brain, and thereby redress the dopamine/acetylcholine imbalance present in Parkinson's disease. Unfortunately, about 70% of patients taking systemically-administered anticholinergics develop serious neuropsychiatric side effects, including hallucinations, dyskinetic movements, and other effects resulting from wide anticholinergic distribution, including vision effects, difficulty swallowing, dry mouth and urine retention. Furthermore, drug treatments may induce undesirable cognitive side effects, such as confusion and/or hallucinations.

Among available treatment options, MAO-B inhibitors prolong the activity of both endogenously- and exogenously-derived dopamine, making them an option either as a monotherapy in early Parkinson's disease or as an adjunctive therapy in patients treated with levodopa who are experiencing motor complications. Selective, irreversible MAO-B inhibitors are recommended due to their safety, tolerability, and easier clinical handling. In addition to symptomatic benefits, experimental data suggest that MAO-B inhibitors may be neuroprotective through MAO-B inhibition and other mechanisms that have yet to be clearly defined. The two available MAO-B inhibitors approved for use in the United States are N-propargylamine derivatives: selegiline (methyl-(1-methyl-2-phenyl-ethyl)-prop-2-ynylamine) and rasagiline (N-propargyl-1-(R)aminoindan). Both selegiline and rasagiline are available in various forms for the treatment of Parkinson's disease. Selegiline is available as conventional tablets, capsules—ELDEPRYL®, extended release films—EMSAM®, orally disintegrating tablets—ZELAPAR®. Rasagiline is available as conventional tablets—AZILECT®, available in 0.5 mg and 1 mg strengths.

Improved treatments for Parkinson's disease are needed, which provide better patient compliance with more convenient dosing and easy-to-administer dosage forms. Furthermore, clinical studies have shown that up to 82% of patients with Parkinson's disease have swallowing difficulties and many such patients tend to dribble. Accordingly, dosage forms like fast-dispersing formulations are particularly preferred since they will disintegrate rapidly in the mouth, thereby minimizing the dosage-administration difficulties, making it easier for patients to take, and making it easier for care-givers to administer. Treatments for Parkinson's disease that make use of different dosage forms have been reported. For example, US 2015/031774, US 2008/107729, US 2004/091525, WO 2009/02084, and US 2012/122993 relate to orally-disintegrating or fast-acting dosage forms.

For Parkinson's disease treatment, maximum benefits are provided during the first few months of medication administration. However, patients taking antiparkinson drugs for a longer period are prone to the "wearing-off" effect, a tendency for the effectiveness of the drug to be lost with time. Hence, the dose of the medication will often have to be increased with time. Moreover, as the dose of the medication is increased, some patients begin to experience side effects, which include anxiety, agitation, dyskinesia, vomiting, low blood pressure, hallucination and nausea, further limiting the treatment options. Sometimes an "on-off effect," where the symptoms become sporadic and unpredictable over a period of time, is also experienced. Additionally, the Parkinson's disease condition itself causes discomfort in holding and/or swallowing dosage form due to involuntary movements, which can severely compromise patient compliance. Considering such factors, a formulation, comprising MAO-B inhibitors like N-propargylamine derivatives, that increases bioavailability and can be administered at lower doses than conventional dosage forms, with similar clinical benefits, is desirable. Such a formulation would increase compliance in those patients who report adverse events after initial treatment with conventional formulations, or who suffer from dysphagia or related swallowing difficulties.

There remains a clear unmet clinical need in the art for dosage forms comprising N-propargylamine derivatives, such as rasagiline, which offer convenient dosing for the patient and allow for reliable and rapid absorption of the drug.

Accordingly, the present application relates to a method of administering N-propargylamine derivatives for the treatment of Parkinson's disease, and a composition for use in the treatment of Parkinson's disease, which provide a convenient oral dosage form that dissolves/disintegrates in the oral cavity of the patient, and which are particularly useful to patients requiring oral medication but have difficulty in swallowing.

SUMMARY OF THE APPLICATION

In an embodiment, the present application relates to a method of treating Parkinson's disease in a patient in need thereof, which comprises administering to the patient a mouth-dissolving composition of rasagiline or a pharmaceutically-acceptable salt thereof.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises a lower dose of rasagiline as compared to commercially-available rasagiline compositions.

In yet another embodiment, the present application relates to a method of treating Parkinson's disease in a patient, which comprises administering to the patient a mouth-dissolving composition of rasagiline or a pharmaceutically-acceptable salt thereof, wherein said composition comprises about a 60% lower dose of rasagiline as compared to commercially-available rasagiline compositions.

In an aspect of the above embodiments, the present method of treating Parkinson's disease in a patient comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof.

In another aspect of the above embodiments, the present method of treating Parkinson's disease in a patient comprises administering to the patient a mouth-dissolving composition of rasagiline or a pharmaceutically-acceptable salt thereof, wherein said composition comprises less than or equal to about 1 mg of rasagiline base.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition has a $T_{lag}$ of not more than about 6 minutes.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition has a $T_{lag}$ of about 5 minutes.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits an $AUC_{0-5\ min}$ of not more than about 130 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits an $AUC_{0-10\ min}$ of not more than about 510 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits an $AUC_{0-20\ min}$ of not more than about 1530 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition exhibits a $T_{max}$ of not more than about 18 minutes.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition when administered to said patients, exhibits at least one of the following pharmacokinetic parameters:

(a) $C_{max}$ of not more than about 7900 pg/ml;
(b) $AUC_{0-t}$ of not more than about 6300 pg·hr/ml; or
(c) $AUC_{0-refTmax}$ of not more than about 1370 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits at least one of the following pharmacokinetic parameters:

(a) $T_{lag}$ of not more than about 6 minutes;
(b) $T_{max}$ of not more than about 18 minutes;
(c) $C_{max}$ of not more than about 7900 pg/ml;
(d) $AUC_{0-5\ min}$ of not more than about 130 pg·hr/ml;
(e) $AUC_{0-10\ min}$ of not more than about 510 pg·hr/ml;
(f) $AUC_{0-20\ min}$ of not more than about 1530 pg·hr/ml;
(g) $AUC_{0-t}$ of not more than about 6300 pg·hr/ml;
(h) $AUC_{0-\infty}$ of not more than about 6400 pg·hr/ml; or
(i) $AUC_{0-refTmax}$ of not more than about 1370 pg·hr/ml.

In an aspect of the above embodiments, the present application relates to a method of treating Parkinson's disease in a patient in need thereof, which comprises administering to the patient a mouth-dissolving composition of N-propargylamine derivative such as rasagiline or a pharmaceutically-acceptable salt thereof, wherein said composition when administered as orally disintegrating dosage form to said patients exhibits bioequivalence to a commercially-available rasagiline composition, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125%, wherein said composition comprises less than or equal to about 1 mg of rasagiline or a pharmaceutically-acceptable salt thereof.

In an aspect of the above embodiments, the present method of treating Parkinson's disease in a patient in need thereof comprises administering to the patient a mouth-dissolving composition of rasagiline or a pharmaceutically-acceptable salt thereof, wherein said composition is administered orally.

In an embodiment, the present method of treating Parkinson's disease in a patient in need thereof comprises administering to the patient a mouth-dissolving composition of rasagiline or a pharmaceutically-acceptable salt thereof, wherein said composition dissolves/disintegrates in less than about 60 seconds in the oral cavity.

In another embodiment, the present application relates to a mouth-dissolving composition of rasagiline or a pharmaceutically-acceptable salt thereof, wherein said composition releases at least about 70% of the rasagiline within about 2 minutes in the oral cavity.

In another embodiment, the present application relates to a mouth-dissolving composition of rasagiline or a pharmaceutically-acceptable salt thereof, wherein said composition releases at least about 70% of the rasagiline within about 2 minutes, when measured in 5 ml of pH 6.75 simulated saliva at 20 rpm and at 37° C.

In another embodiment, the present application relates to a mouth-dissolving composition of rasagiline or a pharmaceutically-acceptable salt thereof, wherein said composition releases at least about 90% of the rasagiline within about 5 minutes, when measured in 5 ml of pH 6.75 simulated saliva at 20 rpm and at 37° C.

In an aspect of the above embodiments, the present mouth-dissolving composition of rasagiline or a pharmaceutically-acceptable salt thereof comprises less than or equal to about 1 mg of rasagiline.

In an aspect of the above embodiments, the mouth-dissolving composition of the present application comprises at least one sugar alcohol and at least one water-swellable polymer.

Examples of sugar alcohols useful in connection with the present application include, but are not limited to, compounds having the general formula $C_nH_{n+2}(OH)_n$, such as mannitol, maltitol, sorbitol, xylitol, lactitol, erythritol, isomalt, threitol and the like, and mixtures thereof. The amount of sugar alcohol that may be used in the present application ranges from about 50% to about 80% by weight of the composition.

Some embodiments of the mouth-dissolving composition of the present application comprise water-swellable polymers in order to dissolve the formulation in the oral cavity. Examples of polymers useful in connection with the present application include, but are not limited to, water-swellable vinyl polymers, including polymers of N-vinylpyrrolidones selected from crospovidone and copovidone; polyvinyl alcohol; polyvinyl acetate; or copolymers or mixtures thereof. The amount of water-swellable vinyl polymers that may be used in the present application ranges from about 0.2% to about 5.0% by weight of the composition.

In an aspect of the above embodiments, the mouth-dissolving composition of the present application comprises at least one sugar alcohol and at least one water-swellable polymer.

In another aspect of the above embodiments, the mouth-dissolving composition of the present application comprises at least one sugar alcohol and two water-swellable polymers.

In an aspect of the above embodiments, the mouth-dissolving composition of the present application comprises sugar alcohols and water-swellable polymers in a weight ratio of from about 2:1 to about 49:1.

The mouth-dissolving composition of the present application optionally comprises at least one pH modifier, such as an acidic pH modifier. Examples of suitable pH modifiers include, but are not limited to, citric acid, tartaric acid, maleic acid, fumaric acid, and succinic acid and the like or mixtures thereof; alkalizers such as meglumine, sodium hydroxide, potassium hydroxide, sodium bicarbonate and the like or mixtures thereof; and buffering agents such as phosphate buffer, acetate buffer, borate buffer and the like or mixtures thereof. Such pH modifiers may be present in an amount of from about 5% to about 7% by weight of the composition.

In an aspect of the above embodiments, the mouth-dissolving composition of the present application provides chemical and physical stability to the composition including a N-propargylamine derivative such as rasagiline or a pharmaceutically-acceptable salt thereof, which does not change the original shape, color, assay values, or composition characteristics, such as impurities, drug concentration, appearance and the like as disclosed herein, wherein the drug is present in an amount of at least about 95% to about 100% of the originally-specified amount and total impurity of not more than about 1.5% for at least about 3 months upon storage at 25° C./60% relative humidity (RH) or at 40° C./75% relative humidity (RH).

DETAILED DESCRIPTION OF THE EMBODIMENTS

Figure 1:
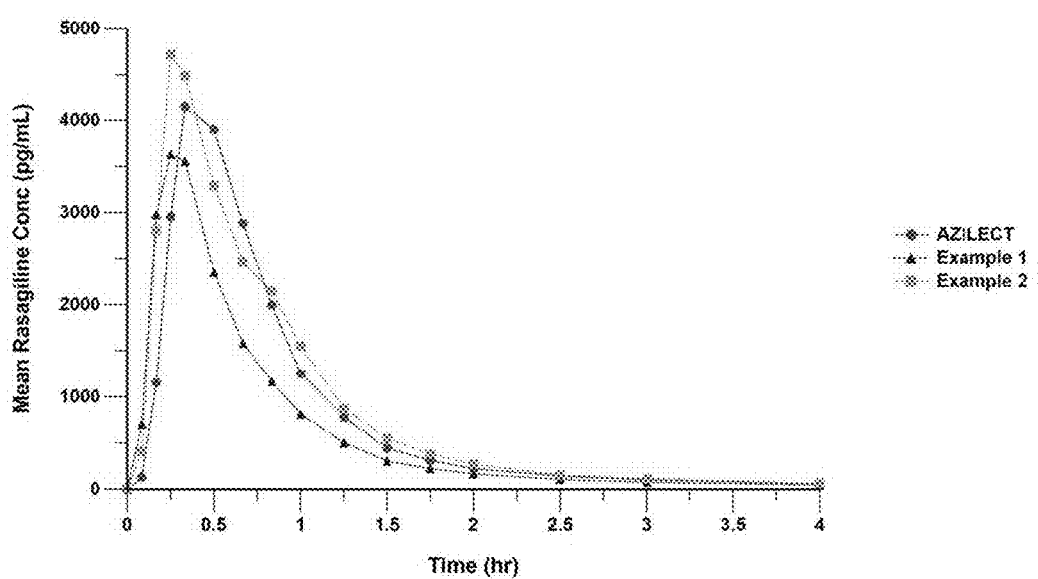
FIG. 1 shows 4-hour plasma rasagiline concentration vs. time profile for an exemplary composition of the present application, as set forth in Examples 1-2, vis-à-vis 1 mg of AZILECT® administered to 18 healthy human subjects in fasting conditions.

The details of one or more embodiments of the present invention are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Definitions

The terms as used herein have the following meanings:

The term "comprising" means the elements recited, or their equivalent in structure or function, plus any other element or elements which are not recited. The terms "having" and "including" are also to be construed as open ended unless the context suggests otherwise. All ranges recited herein include the endpoints, including those that recite a range "between" two values.

The terms "a" and "the" as used herein are understood to encompass the plural as well as the singular or otherwise clearly mentioned wherever needed. For example, reference to "an excipient" includes reference to one or more of such excipients.

The terms such as "about", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value. The term "about" is used to provide flexibility to a numerical range endpoint by providing that a given value may be "a little above" or "a little below" the endpoint. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum.

As used herein, the term "at least" refers to presence of recited substance in the composition in recited least amount.

As used herein, the terms "composition" and "formulation" are used interchangeably and refer to a mixture of two or more compounds, elements, or molecules. Also the terms "composition" and "formulation" may be used to refer to a mixture of one or more active agents with excipients or other carriers.

As used herein, the term "mouth-dissolving composition" can include one or more composition(s) or formulation(s) provided in a format for oral administration, wherein said composition is placed inside the oral cavity of the subject or patient and said composition dissolves or disintegrates in the oral cavity and eases the dosage administration. Such "mouth-dissolving composition" include, sublingual tablets, rapidly disintegrating tablets, buccal tablets, lozenges, caplets, pills, wafers, films, powders, granules, sachets and the like.

The term "disintegrate" is well-understood in the art, and while a composition can be completely disintegrated, the term disintegrate does not necessarily refer to a complete dissolution of the composition, although a dissolved composition (e.g., tablet, lozenge, etc.) would typically be completely disintegrated.

The term "dissolve" is also well-understood in the art. A composition can be completely dissolved, in which there has been a shift from a solid state to a state in which the composition is completely in solution. The term dissolve does not necessarily refer to a completely dissolved composition, and can refer to a state in which the composition is partially dissolved.

The terms "drug" and "pharmaceutical" are used interchangeably to refer to a pharmacologically-active substance or composition. These terms of art are well-known in the pharmaceutical and medicinal arts.

The terms "therapeutically-effective amount" or "effective amount" of a drug as used herein, refers to a non-toxic, but sufficient amount of the drug, to achieve therapeutic results in treating a condition for which the drug is known to be effective. In this instance, an effective amount is an amount of N-propargylamine derivative like rasagiline or a pharmaceutically-acceptable salt thereof, approximately less than or equal to about 1 mg, which is sufficient to treat the patients with Parkinson's disease or its associated conditions, but low enough to avoid serious side effects (at a reasonable benefit/risk ratio), within the scope of sound medical judgment. The effective amount of said N-propargylamine derivative will vary with the particular condition being treated, the age and physical condition of the patient being treated, the severity of the condition, the duration of the treatment, the nature of concurrent therapy, and like factors within the knowledge and expertise of the attending physician.

As used herein, the term "patient" refers to a target of administration. The patient can be human or non-human, and thus the composition and method disclosed herein can be used for both human treatment and for veterinary therapeutic uses. As used herein, the terms "administering" and "administration" refer to the act of providing a composition to a patient, e.g., oral administration.

The term "excipients" or "carriers" as used herein, refers to any pharmaceutically-acceptable materials suitable for preparing composition or formulation as disclosed herein, which are nontoxic and do not interact with other components of a composition in a deleterious manner.

The term, "Parkinson's disease" as used herein, refers to which include, but are not limited to tremor, bradykinesia, muscle rigidity or a disturbance of posture. This term also refers to a syndrome which resembles Parkinson's disease, but which may or may not be caused by Parkinson's disease, such as parkinsonian-like side effects caused by certain antipsychotic drugs and other such symptoms.

The term "N-propargylamine derivative" as used herein, is intended to include, but not limited to, selegiline (methyl-(1-methyl-2-phenyl-ethyl)-prop-2-ynyl-amine), rasagiline (N-propargyl-1-(R)aminoindan) and pharmacologically active derivatives of N-propargylamine, including both individual enantiomers of N-propargylamine (dextrogyral and levogyral enantiomers) in their substantially pure form and their pharmaceutically-acceptable salts, mixtures (in any ratio) of N-propargylamine enantiomers and their pharmaceutically-acceptable salts, and active metabolites of N-propargylamine and their pharmaceutically-acceptable salts. The solid state form of N-propargylamine used in the composition is not critical. For example, N-propargylamine can be amorphous or crystalline.

The term "pharmaceutically-acceptable salt(s)" as used herein, includes those salts which are, within the scope of sound medical judgment, suitable for use in contact with the tissues of humans and lower animals without undue toxicity, irritation, allergic response and the like, which are well known in the art. The salts can be prepared in situ during the final isolation and purification of the compounds of the invention, or separately by reacting the pharmaceutically active substance having a free base function with a suitable organic acid or inorganic acid. Examples of pharmaceutically-acceptable salts include, but not limited to, any of the salts or co-crystals of N-propargylamine selected from mesylate, citrate, tartrate, fumarate, besylate, ethyl sulfonate, sulfate, hydrochloride and the like. The salts may be in the form of solvate, hydrate, hemihydrates or anhydrous forms.

The term "$T_{lag}$" as used herein refers to time delay between administration of the composition and first observed drug concentration in plasma, which is within a limit of quantification.

The term "d(90)," as used herein refers to a granule diameter at which 90% of granules present in the composition have diameters less than about 250µ.

The term "d(50)," as used herein, refers to a granule diameter at which 50% of granules present in the composition have diameters less than about 75µ.

The term "$C_{max}$" is well-understood in the art and refers to the pharmacokinetic parameter that is the maximum observed concentration, occurring at $T_{max}$. The term "$T_{max}$" is also well-understood in the art and refers to the time of maximum observed concentration following administration.

The term "$AUC_{0-t}$" as used herein refers to the area under the curve (AUC) from the time of administration (0) to the time of observation (t), and is a pharmacokinetic parameter well-understood by those of ordinary skill in the art. Accordingly, the term "$AUC_{0-refTmax}$" refers to the AUC from the time of administration to the time of maximum observed concentration.

The term "stable" as used herein, refers to a chemical and physical stability of the present pharmaceutical composition including N-propargylamine derivative like rasagiline or a pharmaceutically-acceptable salt thereof, which does not change original shape, color, assay values and composition characteristics such as impurities, drug concentration, appearance and the like as disclosed herein, wherein the drug is present in an amount of at least about 95% to about 100% of the originally specified amount and total impurity of not more than about 1.5% for at least about 3 months upon storage at 25° C./60% relative humidity (RH) or at 40° C./75% relative humidity (RH).

The term "commercially-available rasagiline composition" as used herein, refers to AZILECT® oral tablets containing rasagiline mesylate or its pharmaceutical equivalents or its therapeutic equivalents or later approved drugs which are designated as AB rated by US FDA as per Approved Drug Products with Therapeutic Equivalence Evaluations (34th edition) or drugs having obtained marketing approval by US FDA through Abbreviated New Drug Application (ANDA) filing by establishing bioequivalence to such Product. For example, in some embodiments, AZILECT® includes compressed tablet of rasagiline mesylate equivalent to 0.5 mg or 1 mg of rasagiline base along with excipients such as mannitol, starch, pregelatinized starch, colloidal silicon dioxide, stearic acid and talc. In some embodiments AZILECT® includes its US FDA approved therapeutic or pharmaceutical equivalents. AZILECT® is marketed TEVA Neuroscience, Inc., Overland Park, Kans. 66211.

In an embodiment, the present application relates to a method of treating Parkinson's disease in a patient in need thereof, which comprises administering to the patient a mouth-dissolving composition of N-propargylamine derivative or a pharmaceutically-acceptable salt thereof.

In another embodiment, the present application relates to a method of treating Parkinson's disease in a patient in need thereof, which comprises administering to the patient a mouth-dissolving composition of rasagiline or a pharmaceutically-acceptable salt thereof.

In another embodiment, the present application relates to a method of treating Parkinson's disease in a patient in need thereof, which comprises administering to the patient a mouth-dissolving composition of N-propargylamine derivative or a pharmaceutically-acceptable salt thereof, wherein said composition comprises a lower dose of N-propargylamine derivative as compared to commercially-available N-propargylamine derivative composition.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises a lower dose of rasagiline as compared to commercially-available rasagiline compositions.

In an aspect of the above embodiment, the present method of treating Parkinson's disease in a patient comprises administering a lower dose of rasagiline, wherein said lower dose is less than about 5%, 10%, 15%, 20%, 25%, 30%, 35%, 40%, 45%, 50%, 55% or 60% of the rasagiline as compared to commercially-available rasagiline compositions.

In an embodiment, the present application relates to a method of treating Parkinson's disease in a patient comprising administering to the patient a mouth-dissolving composition of rasagiline or a pharmaceutically-acceptable salt thereof, wherein said composition comprises about a 10% lower dose of rasagiline as compared to commercially-available rasagiline compositions.

In another embodiment, the present application relates to a method of treating Parkinson's disease in a patient comprising administering to the patient a mouth-dissolving composition of rasagiline or a pharmaceutically-acceptable salt thereof, wherein said composition comprises about a 20% lower dose of rasagiline as compared to commercially-available rasagiline compositions.

In another embodiment, the present application relates to a method of treating Parkinson's disease in a patient comprising administering to the patient a mouth-dissolving composition of rasagiline or a pharmaceutically-acceptable salt thereof, wherein said composition comprises about a 30% lower dose of rasagiline as compared to commercially-available rasagiline compositions.

In another embodiment, the present application relates to a method of treating Parkinson's disease in a patient comprising administering to the patient a mouth-dissolving composition of rasagiline or a pharmaceutically-acceptable salt thereof, wherein said composition comprises about a 40% lower dose of rasagiline as compared to commercially-available rasagiline compositions.

In another embodiment, the present application relates to a method of treating Parkinson's disease in a patient comprising administering to the patient a mouth-dissolving composition of rasagiline or a pharmaceutically-acceptable salt thereof, wherein said composition comprises about a 50% lower dose of rasagiline as compared to commercially-available rasagiline compositions.

In another embodiment, the present application relates to a method of treating Parkinson's disease in a patient comprising administering to the patient a mouth-dissolving composition of rasagiline or a pharmaceutically-acceptable salt thereof, wherein said composition comprises about a 60% lower dose of rasagiline as compared to commercially-available rasagiline compositions.

In an aspect of the above embodiments, the present method of treating Parkinson's disease in a patient comprises administering to the patient a mouth-dissolving composition of N-propargylamine derivative or a pharmaceutically-acceptable salt thereof, wherein said composition comprises less than or equal to about 1 mg of N-propargylamine derivative or a pharmaceutically-acceptable salt thereof.

In an aspect of the above embodiments, the present method of treating Parkinson's disease in a patient comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof.

In another aspect of the above embodiments, the present method of treating Parkinson's disease in a patient in need thereof comprises administering to the patient a mouth-dissolving composition of rasagiline or a pharmaceutically-acceptable salt thereof, wherein said composition comprises less than about 1 mg of rasagiline or a pharmaceutically-acceptable salt thereof.

In yet another aspect of the above embodiments, the present method of treating Parkinson's disease in a patient in need thereof comprises administering to the patient a mouth-dissolving composition of rasagiline or a pharmaceutically-acceptable salt thereof, wherein said composition comprises about 1.0 mg, 0.9 mg, 0.8 mg, 0.7 mg, 0.6 mg, 0.5 mg, 0.4 mg or 0.3 mg of rasagiline or a pharmaceutically-acceptable salt thereof.

In yet another aspect of the above embodiments, the present method of treating Parkinson's disease in a patient in need thereof comprises administering to the patient a mouth-dissolving composition of rasagiline or a pharmaceutically-acceptable salt thereof, wherein said composition comprises about 0.9 mg, 0.8 mg, 0.7 mg, 0.6 mg, 0.5 mg, 0.4 mg or 0.3 mg of rasagiline base.

In an embodiment, the present application relates to a method of treating Parkinson's disease in a patient in need thereof, which comprises administering to the patient a mouth-dissolving composition of N-propargylamine derivative or a pharmaceutically-acceptable salt thereof, wherein said composition upon administration exhibits $T_{lag}$ of not more than about 6 minutes.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $T_{lag}$ of not more than about 6 minutes.

In another aspect of the above embodiments, the present application relates to a method of treating Parkinson's disease in a patient in need thereof, which comprises administering to the patient a mouth-dissolving composition of N-propargylamine derivative or a pharmaceutically-acceptable salt thereof, wherein said composition upon administration exhibits $T_{lag}$ of about 5 minutes.

In another aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $T_{lag}$ of about 5 minutes.

In one embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $T_{max}$ of not more than about 18 minutes.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $T_{max}$ ranging from about 12 minutes to about 18 minutes.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $C_{max}$ of not more than about 7900 pg/ml.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $C_{max}$ ranging from about 3420 pg/ml to about 7900 pg/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-5\ min}$ of not more than about 130 pg·hr/ml.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-5\ min}$ ranging from about 60 pg·hr/ml to about 130 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-10\ min}$ of not more than about 510 pg·hr/ml.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition exhibits $AUC_{0-10\ min}$ ranging from about 175 pg·hr/ml to about 510 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-20\ min}$ of not more than about 1530 pg·hr/ml.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-20\ min}$ ranging from about 1000 pg·hr/ml to about 1530 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-t}$ of not more than about 6300 pg·hr/ml.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-t}$ ranging from about 3200 pg·hr/ml to about 6300 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-\infty}$ of not more than about 6400 pg·hr/ml.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-\infty}$ ranging from about 2200 pg·hr/ml to about 6400 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-refTmax}$ of not more than about 1370 pg·hr/ml.

In an aspect of the above embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits $AUC_{0-refTmax}$ ranging from about 770 pg·hr/ml to about 1370 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits at least one of the following pharmacokinetic parameters:
 (a) $C_{max}$ of not more than about 7900 pg/ml;
 (b) $AUC_{0-t}$ of not more than about 6300 pg·hr/ml; or
 (c) $AUC_{0-refTmax}$ of not more than about 1370 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits at least one of the following pharmacokinetic parameters:
 (a) $C_{max}$ from about 3420 pg/ml to about 7900 pg/ml;
 (b) $AUC_{0-t}$ from about 3200 pg·hr/ml to about 6300 pg·hr/ml; or
 (c) $AUC_{0-refTmax}$ from about 770 pg·hr/ml to about 1370 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits at least one of the following pharmacokinetic parameters:
 (a) $T_{lag}$ of not more than about 6 minutes;
 (b) $T_{max}$ of not more than about 18 minutes;
 (c) $C_{max}$ of not more than about 7900 pg/ml;
 (d) $AUC_{0-5\ min}$ of not more than about 130 pg·hr/ml;
 (e) $AUC_{0-10\ min}$ of not more than about 510 pg·hr/ml;
 (f) $AUC_{0-20\ min}$ of not more than about 1530 pg·hr/ml;
 (g) $AUC_{0-t}$ of not more than about 6300 pg·hr/ml;
 (h) $AUC_{0-\infty}$ of not more than about 6400 pg·hr/ml; or
 (i) $AUC_{0-refTmax}$ of not more than about 1370 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits at least one of the following pharmacokinetic parameters:
 (a) $T_{lag}$ from about 2 minutes to about 6 minutes;
 (b) $T_{max}$ from about 12 minutes to about 18 minutes;
 (c) $C_{max}$ from about 3420 pg/ml to about 7900 pg/ml;
 (d) $AUC_{0-5\ min}$ from about 60 pg·hr/ml to about 130 pg·hr/ml;
 (e) $AUC_{0-10\ min}$ from about 175 pg·hr/ml to about 510 pg·hr/ml;
 (f) $AUC_{0-20\ min}$ from about 1000 pg·hr/ml to about 1530 pg·hr/ml;
 (g) $AUC_{0-t}$ from about 3200 pg·hr/ml to about 6300 pg·hr/ml;
 (h) $AUC_{0-\infty}$ from about 2200 pg·hr/ml to about 6400 pg·hr/ml; or
 (i) $AUC_{0-refTmax}$ from about 770 pg·hr/ml to about 1370 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and upon administration exhibits at least one of the following pharmacokinetic parameters:
 (a) $C_{max}$ from about 3420 pg/ml to about 7900 pg/ml;
 (b) $AUC_{0-t}$ from about 3200 pg·hr/ml to about 6300 pg·hr/ml; or
 (c) $AUC_{0-refTmax}$ from about 770 pg·hr/ml to about 1370 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and upon administration exhibits at least one of the following pharmacokinetic parameters:
 (a) $T_{lag}$ from about 2 minutes to about 6 minutes;
 (b) $T_{max}$ from about 12 minutes to about 18 minutes;
 (c) $C_{max}$ from about 3420 pg/ml to about 7900 pg/ml;
 (d) $AUC_{0-5\ min}$ from about 60 pg·hr/ml to about 130 pg·hr/ml;
 (e) $AUC_{0-10\ min}$ from about 175 pg·hr/ml to about 510 pg·hr/ml;
 (f) $AUC_{0-20\ min}$ from about 1000 pg·hr/ml to about 1530 pg·hr/ml;

(g) $AUC_{0-t}$ from about 3200 pg·hr/ml to about 6300 pg·hr/ml;
(h) $AUC_{0-\infty}$ from about 2200 pg·hr/ml to about 6400 pg·hr/ml; or
(d) $AUC_{0-refTmax}$ from about 770 pg·hr/ml to about 1370 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises less than 1 mg of rasagiline or a pharmaceutically-acceptable salt thereof and upon administration exhibits at least one of the following pharmacokinetic parameters:
 (a) $T_{lag}$ of not more than about 6 minutes;
 (b) $T_{max}$ of not more than about 18 minutes;
 (c) $C_{max}$ of not more than about 6600 pg/ml;
 (d) $AUC_{0-5\ min}$ of not more than about 80 pg·hr/ml;
 (e) $AUC_{0-10\ min}$ of not more than about 410 pg·hr/ml;
 (f) $AUC_{0-20\ min}$ of not more than about 1370 pg·hr/ml;
 (g) $AUC_{0-t}$ of not more than about 5010 pg·hr/ml;
 (h) $AUC_{0-\infty}$ of not more than about 5090 pg·hr/ml; or
 (e) $AUC_{0-refTmax}$ of not more than about 1370 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than 1 mg of rasagiline or a pharmaceutically-acceptable salt thereof and upon administration exhibits at least one of the following pharmacokinetic parameters:
 (a) $T_{lag}$ from about 2 minutes to about 6 minutes;
 (b) $T_{max}$ from about 12 minutes to about 18 minutes;
 (c) $C_{max}$ from about 3420 pg/ml to about 6600 pg/ml;
 (d) $AUC_{0-5\ min}$ from about 60 pg·hr/ml to about 80 pg·hr/ml;
 (e) $AUC_{0-10\ min}$ from about 130 pg·hr/ml to about 410 pg·hr/ml;
 (f) $AUC_{0-20\ min}$ from about 1000 pg·hr/ml to about 1370 pg·hr/ml;
 (g) $AUC_{0-t}$ from about 2220 pg·hr/ml to about 5010 pg·hr/ml;
 (h) $AUC_{0-\infty}$ from about 2140 pg·hr/ml to about 5090 pg·hr/ml; or
 (f) $AUC_{0-refTmax}$ from about 770 pg·hr/ml to about 1370 pg·hr/ml.

In an aspect of the above embodiments, the present application relates to a method of treating Parkinson's disease in a patient in need thereof, which comprises sublingually administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and upon sublingual administration exhibits at least one of the following pharmacokinetic parameters:
 (a) $T_{lag}$ from about 2 minutes to about 6 minutes;
 (b) $T_{max}$ from about 12 minutes to about 18 minutes;
 (c) $C_{max}$ from about 3420 pg/ml to about 7900 pg/ml;
 (d) $AUC_{0-5\ min}$ from about 60 pg·hr/ml to about 130 pg·hr/ml;
 (e) $AUC_{0-10\ min}$ from about 175 pg·hr/ml to about 510 pg·hr/ml;
 (f) $AUC_{0-20\ min}$ from about 1000 pg·hr/ml to about 1530 pg·hr/ml;
 (g) $AUC_{0-t}$ from about 3200 pg·hr/ml to about 6300 pg·hr/ml;
 (h) $AUC_{0-\infty}$ from about 2200 pg·hr/ml to about 6400 pg·hr/ml; or
 (g) $AUC_{0-refTmax}$ from about 770 pg·hr/ml to about 1370 pg·hr/ml.

In an embodiment, the present application relates to a method of treating Parkinson's disease in a patient in need thereof, which comprises sublingually administering to the patient a mouth-dissolving composition of rasagiline or a pharmaceutically-acceptable salt thereof, wherein said composition comprises less than 1 mg of rasagiline or a pharmaceutically-acceptable salt thereof and upon sublingual administration exhibits at least one of the following pharmacokinetic parameters:
 (a) $T_{lag}$ of not more than about 6 minutes;
 (b) $T_{max}$ of not more than about 18 minutes;
 (c) $C_{max}$ of not more than about 6600 pg/ml;
 (d) $AUC_{0-5\ min}$ of not more than about 80 pg·hr/ml;
 (e) $AUC_{0-10\ min}$ of not more than about 410 pg·hr/ml;
 (f) $AUC_{0-20\ min}$ of not more than about 1370 pg·hr/ml;
 (g) $AUC_{0-t}$ of not more than about 5010 pg·hr/ml;
 (h) $AUC_{0-\infty}$ of not more than about 5090 pg·hr/ml; or
 (i) $AUC_{0-refTmax}$ of not more than about 1370 pg·hr/ml.

In an embodiment, the present application relates to a method of treating Parkinson's disease in a patient in need thereof, which comprises sublingually administering to the patient a mouth-dissolving composition of rasagiline or a pharmaceutically-acceptable salt thereof, wherein said composition comprises about 0.6 mg of rasagiline base and upon sublingual administration exhibits at least one of the following pharmacokinetic parameters:
 (a) $T_{lag}$ of not more than about 6 minutes;
 (b) $T_{max}$ of not more than about 18 minutes;
 (c) $C_{max}$ of not more than about 6600 pg/ml;
 (d) $AUC_{0-5\ min}$ of not more than about 80 pg·hr/ml;
 (e) $AUC_{0-10\ min}$ of not more than about 410 pg·hr/ml;
 (f) $AUC_{0-20\ min}$ of not more than about 1370 pg·hr/ml;
 (g) $AUC_{0-t}$ of not more than about 5010 pg·hr/ml;
 (h) $AUC_{0-\infty}$ of not more than about 5090 pg·hr/ml; or
 (i) $AUC_{0-refTmax}$ of not more than about 1370 pg·hr/ml.

In an embodiment, the present application relates to a method of treating Parkinson's disease in a patient in need thereof, which comprises sublingually administering to the patient a mouth-dissolving composition of rasagiline or a pharmaceutically-acceptable salt thereof, wherein said composition comprises about 0.6 mg of rasagiline base and upon sublingual administration exhibits at least one of the following pharmacokinetic parameters:
 (a) $T_{lag}$ of not more than about 6 minutes;
 (b) $T_{max}$ of not more than about 15 minutes;
 (c) $C_{max}$ of not more than about 6600 pg/ml;
 (d) $AUC_{0-5\ min}$ of not more than about 80 pg·hr/ml;
 (e) $AUC_{0-10\ min}$ of not more than about 410 pg·hr/ml;
 (f) $AUC_{0-20\ min}$ of not more than about 1370 pg·hr/ml;
 (g) $AUC_{0-t}$ of not more than about 5010 pg·hr/ml;
 (h) $AUC_{0-\infty}$ of not more than about 5090 pg·hr/ml; or
 (i) $AUC_{0-refTmax}$ of not more than about 1370 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises about 1 mg of rasagiline or a pharmaceutically-acceptable salt thereof and when administered as orally disintegrating dosage form exhibits at least one of the following pharmacokinetic parameters:

(a) $T_{lag}$ of not more than about 6 minutes;
(b) $T_{max}$ of not more than about 18 minutes;
(c) $C_{max}$ of not more than about 7900 pg/ml;
(d) $AUC_{0-5\ min}$ of not more than about 130 pg·hr/ml;
(e) $AUC_{0-10\ min}$ of not more than about 510 pg·hr/ml;
(f) $AUC_{0-20\ min}$ of not more than about 1530 pg·hr/ml;
(g) $AUC_{0-t}$ of not more than about 6300 pg·hr/ml; or
(h) $AUC_{0-\infty}$ of not more than about 6390 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises about 1 mg of rasagiline or a pharmaceutically-acceptable salt thereof and when administered as orally disintegrating dosage form exhibits at least one of the following pharmacokinetic parameters:
(a) $T_{lag}$ from about 2 minutes to about 6 minutes;
(b) $T_{max}$ from about 12 minutes to about 18 minutes;
(c) $C_{max}$ from about 5840 pg/ml to about 7900 pg/ml;
(d) $AUC_{0-5\ min}$ from about 95 pg·hr/ml to about 130 pg·hr/ml;
(e) $AUC_{0-10\ min}$ from about 380 pg·hr/ml to about 510 pg·hr/ml;
(f) $AUC_{0-20\ min}$ from about 1130 pg·hr/ml to about 1530 pg·hr/ml;
(g) $AUC_{0-t}$ from about 4650 pg·hr/ml to about 6300 pg·hr/ml; or
(h) $AUC_{0-\infty}$ from about 4720 pg·hr/ml to about 6390 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises about 1 mg of rasagiline base and when administered as orally disintegrating dosage form exhibits at least one of the following pharmacokinetic parameters:
(a) $T_{lag}$ from about 2 minutes to about 6 minutes;
(b) $T_{max}$ from about 12 minutes to about 18 minutes;
(c) $C_{max}$ from about 5840 pg/ml to about 7900 pg/ml;
(d) $AUC_{0-5\ min}$ from about 95 pg·hr/ml to about 130 pg·hr/ml;
(e) $AUC_{0-10\ min}$ from about 380 pg·hr/ml to about 510 pg·hr/ml;
(f) $AUC_{0-20\ min}$ from about 1130 pg·hr/ml to about 1530 pg·hr/ml;
(g) $AUC_{0-t}$ from about 4650 pg·hr/ml to about 6300 pg·hr/ml; or
(h) $AUC_{0-\infty}$ from about 4720 pg·hr/ml to about 6390 pg·hr/ml.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises about 1 mg of rasagiline base and when administered as orally disintegrating dosage form exhibits at least one of the following pharmacokinetic parameters:
(a) $T_{lag}$ from about 2 minutes to about 6 minutes;
(b) $T_{max}$ from about 12 minutes to about 15 minutes;
(c) $C_{max}$ from about 5840 pg/ml to about 7900 pg/ml;
(d) $AUC_{0-5\ min}$ from about 95 pg·hr/ml to about 130 pg·hr/ml;
(e) $AUC_{0-10\ min}$ from about 380 pg·hr/ml to about 510 pg·hr/ml;
(f) $AUC_{0-20\ min}$ from about 1130 pg·hr/ml to about 1530 pg·hr/ml;
(g) $AUC_{0-t}$ from about 4650 pg·hr/ml to about 6300 pg·hr/ml; or
(h) $AUC_{0-\infty}$ from about 4720 pg·hr/ml to about 6390 pg·hr/ml.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits about 3.0 fold higher $AUC_{0-5\ min}$ in comparison to commercially-available rasagiline composition.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and upon administration exhibits about 3.0 fold higher $AUC_{0-5\ min}$ in comparison to commercially-available rasagiline composition.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits about 3.0 to about 7.0 fold higher $AUC_{0-10\ min}$ in comparison to commercially-available rasagiline composition.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and upon administration exhibits about 3.0 to about 7.0 fold higher $AUC_{0-10\ min}$ in comparison to commercially-available rasagiline composition.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits about 3.0 fold higher $AUC_{0-10\ min}$ in comparison to commercially-available rasagiline composition.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and upon administration exhibits about 3.0 fold higher $AUC_{0-10\ min}$ in comparison to commercially-available rasagiline composition.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition when administered as orally disintegrating dosage form exhibits about 7.0 fold higher $AUC_{0-10\ min}$ in comparison to commercially-available rasagiline composition.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and when administered as orally disintegrating dosage form exhibits about 7.0 fold higher $AUC_{0-10\ min}$ in comparison to commercially-available rasagiline composition.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition upon administration exhibits bioequivalence to a commercially-available rasagiline composition, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125%.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof, upon administration exhibits bioequivalence to a commercially-available rasagiline composition, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$.

In an aspect of the above embodiments, the present application relates to a method of treating Parkinson's disease in a patient in need thereof, which comprises sublingually administering to the patient a mouth-dissolving composition of rasagiline or a pharmaceutically-acceptable salt thereof, wherein said composition upon administration exhibits bioequivalence to a commercially-available rasagiline composition, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125%.

In an aspect of the above embodiments, the present application relates to a method of treating Parkinson's disease in a patient in need thereof, which comprises sublingually administering to the patient a mouth-dissolving composition of rasagiline or a pharmaceutically-acceptable salt thereof, wherein said composition comprises less than 1 mg of rasagiline or a pharmaceutically-acceptable salt thereof and upon administration exhibits bioequivalence to a commercially-available rasagiline composition, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125%.

In an aspect of the above embodiments, the present application relates to a method of treating Parkinson's disease in a patient in need thereof, which comprises sublingually administering to the patient a mouth-dissolving composition of rasagiline or a pharmaceutically-acceptable salt thereof, wherein said composition comprises 0.6 mg of rasagiline base and upon administration exhibits bioequivalence to a commercially-available rasagiline composition comprising 1.0 mg of rasagiline base, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125%.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition when administered as orally disintegrating dosage form exhibits bioequivalence to a commercially-available rasagiline composition, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than 1 mg of rasagiline or a pharmaceutically-acceptable salt thereof and when administered as orally disintegrating dosage form exhibits bioequivalence to a commercially-available rasagiline composition, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises about 1 mg of rasagiline base and when administered as orally disintegrating dosage form exhibits bioequivalence to a commercially-available rasagiline composition comprising 1.0 mg of rasagiline base, and said bioequivalence is established by: (a) a 90% Confidence Interval for mean $C_{max}$, which is between 80% and 125%, (b) a 90% Confidence Interval for mean $AUC_{0-t}$, which is between 80% and 125% and (c) a 90% Confidence Interval for mean $AUC_{0-\infty}$, which is between 80% and 125.

In an aspect of the above embodiments, the present method of treating Parkinson's disease in a patient in need thereof comprises administering to the patient a mouth-dissolving composition of N-propargylamine derivative or a pharmaceutically-acceptable salt thereof, wherein said composition is administered orally.

In another aspect of the above embodiments, the present method of treating Parkinson's disease in a patient in need thereof comprises administering to the patient a mouth-dissolving composition comprising N-propargylamine derivative such as rasagiline or selegiline or a pharmaceutically-acceptable salt thereof, wherein said composition is administered orally.

In an aspect of the above embodiments, the present method of treating Parkinson's disease in a patient in need thereof comprises administering to the patient a mouth-dissolving composition of rasagiline or a pharmaceutically-acceptable salt thereof, wherein said composition is administered orally.

In an aspect of the above embodiments, the rasagiline or a pharmaceutically-acceptable salt thereof used in the present application include, but not limited to, pharmaceutically-acceptable, pharmacologically active derivatives of rizatriptan, including both individual enantiomers of rasagiline (dextrogyral and levogyral enantiomers) in their substantially pure form and their pharmaceutically-acceptable salts, mixtures (in any ratio) of rasagiline enantiomers and their pharmaceutically-acceptable salts, and active metabolites of rasagiline and their pharmaceutically-acceptable salts. The solid state form of rasagiline used in the composition is not critical. For example, rasagiline can be amorphous or crystalline. Examples of pharmaceutically-acceptable salts include, but not limited to, any of the salts or co-crystals of rasagiline selected from mesylate, hydrochloride, hydrobromide, citrate, benzoate, sulphate, phosphate, maleate, formate, acetate, nitrate, succinate and the like. The salts may be in the form of solvate, hydrate, hemihydrates or anhydrous forms. The amount of pharmaceutically-acceptable rasagiline salt used in the present composition is equivalent or less than about 1 mg of rasagiline base. For example, 0.6 mg of rasagiline base is equivalent to 0.936 mg of rasagiline mesylate.

In an embodiment, the present application relates to a mouth-dissolving composition of rasagiline or a pharmaceutically-acceptable salt thereof, wherein said composition has enhanced bioavailability in comparison to commercially-available rasagiline composition.

In an embodiment, the present application relates to a method of treating Parkinson's disease in a patient in need thereof, which comprises administering to the patient a mouth-dissolving composition of rasagiline or a pharmaceutically-acceptable salt thereof, wherein said composition has enhanced bioavailability in comparison to commercially-available rasagiline composition.

In an aspect of the above embodiments, the present method of treating Parkinson's disease in a patient in need thereof comprises administering to the patient a mouth-dissolving composition of rasagiline or a pharmaceutically-acceptable salt thereof, wherein said composition dissolves/disintegrates in less than about 60, 50, 40, 30 or 20 seconds in the oral cavity.

In an embodiment, the present method of treating Parkinson's disease in a patient in need thereof comprises administering to the patient a mouth-dissolving composition of rasagiline or a pharmaceutically-acceptable salt thereof, wherein said composition dissolves/disintegrates in less than about 60 seconds in the oral cavity.

In another embodiment, the present application relates to a mouth-dissolving composition of rasagiline or a pharmaceutically-acceptable salt thereof, wherein said composition releases at least about 70% of the rasagiline within about 2 minutes in the oral cavity.

In another embodiment, the present application relates to a mouth-dissolving composition of rasagiline or a pharmaceutically-acceptable salt thereof, wherein said composition releases at least about 90% of the rasagiline within about 5 minutes in the oral cavity.

In another embodiment, the present application relates to a mouth-dissolving composition of rasagiline or a pharmaceutically-acceptable salt thereof, wherein said composition releases at least about 70% of the rasagiline within about 2 minutes, when measured in 5 ml of pH 6.75 simulated saliva at 20 rpm and at 37° C.

In another embodiment, the present application relates to a mouth-dissolving composition of rasagiline or a pharmaceutically-acceptable salt thereof, wherein said composition releases at least about 90% of the rasagiline within about 5 minutes when measured in 5 ml of pH 6.75 simulated saliva at 20 rpm and at 37° C.

In an aspect of the above embodiments, the present mouth-dissolving composition of rasagiline or a pharmaceutically-acceptable salt thereof comprises less than or equal to about 1 mg of rasagiline base.

In an aspect of the above embodiments, the present mouth-dissolving composition of rasagiline or a pharmaceutically-acceptable salt thereof comprises less than about 1.0 mg, 0.9 mg, 0.8 mg, 0.7 mg, 0.6 mg, 0.5 mg, 0.4 mg or 0.3 mg of rasagiline.

In an aspect of the above embodiments, the present mouth-dissolving composition of rasagiline or a pharmaceutically-acceptable salt thereof comprises about 0.8 mg, 0.6 mg or 0.4 mg of rasagiline base.

In an aspect of the above embodiments, the present mouth-dissolving composition of rasagiline or a pharmaceutically-acceptable salt thereof comprises about 1 mg of rasagiline.

In one embodiment, the present method of treating Parkinson's disease in a patient in need thereof comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof and dissolves/disintegrates in less than about 60 seconds in the oral cavity.

In another embodiment, the present application relates to a mouth-dissolving composition of rasagiline or a pharmaceutically-acceptable salt thereof, wherein said composition comprises less than or equal to about 1 mg of rasagiline or a pharmaceutically-acceptable salt thereof and releases at least about 70% of the rasagiline within about 2 minutes in the oral cavity.

In another embodiment, the present application relates to a mouth-dissolving composition of rasagiline or a pharmaceutically-acceptable salt thereof, wherein said composition comprises less than or equal to about 1 mg of rasagiline or a pharmaceutically-acceptable salt thereof and releases at least about 90% of the rasagiline within about 5 minutes in the oral cavity.

In another embodiment, the present application relates to a mouth-dissolving composition of rasagiline or a pharmaceutically-acceptable salt thereof, wherein said composition comprises less than or equal to about 1 mg of rasagiline or a pharmaceutically-acceptable salt thereof and releases at least about 70% of the rasagiline within about 2 minutes, when measured in 5 ml of pH 6.75 simulated saliva at 20 rpm and at 37° C.

In another embodiment, the present application relates to a mouth-dissolving composition of rasagiline or a pharmaceutically-acceptable salt thereof, wherein said composition comprises less than or equal to about 1 mg of rasagiline or a pharmaceutically-acceptable salt thereof and releases at least about 90% of the rasagiline within about 5 minutes when measured in 5 ml of pH 6.75 simulated saliva at 20 rpm and at 37° C.

The mouth-dissolving composition of the present application comprises at least one sugar alcohol, in order to dissolve the formulation in the oral cavity. Some of the examples of sugar alcohol used in the present application include, but are not limited to, the compound having general formula $C_nH_{n+2}(OH)_n$ such as mannitol, maltitol, sorbitol, xylitol, lactitol, erythritol, isomalt, threitol and the like or mixtures thereof. The amount of sugar alcohol that may be used in the present application ranges from about 50% to about 80% by weight of the composition.

The mouth-dissolving composition of the present application comprises water-swellable polymers, in order to dissolve the formulation in the oral cavity. Some of the examples of such polymers used in the present application include, but are not limited to, water-swellable vinyl polymers like polymers of N-vinylpyrrolidone selected from crospovidone, copovidone; polyvinyl alcohol, polyvinyl acetate; or copolymers or mixtures thereof. Such water-swellable vinyl polymers are present in an amount of from about 0.2% to about 5.0% by weight of the composition.

In an aspect of the above embodiments, the mouth-dissolving composition of the present application comprises at least one sugar alcohol and at least one water-swellable polymer.

In another aspect of the above embodiments, the mouth-dissolving composition of the present application comprises at least one sugar alcohol and two water-swellable polymers.

In an aspect of the above embodiments, the mouth-dissolving composition of the present application comprises sugar alcohol and water-swellable polymers are present in a weight ratio of from about 2:1 to about 49:1.

In one embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises therapeutically effective amount of rasagiline or a pharmaceutically-acceptable salt thereof, at least one sugar alcohol and at least one water-swellable polymer.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises therapeutically effective amount of rasagiline or a pharmaceutically-acceptable salt thereof, at least one sugar alcohol and at least two water-swellable polymers.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises therapeutically effective amount of rasagiline or a pharmaceutically-acceptable salt thereof, at least one sugar alcohol and at least one water-swellable polymer, and said sugar alcohol and water-swellable polymers are present in a weight ratio of from about 2:1 to about 49:1.

In one embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof, at least one sugar alcohol and at least one water-swellable polymer.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof, at least one sugar alcohol and at least two water-swellable polymers.

In an aspect of the above embodiments, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof, at least one sugar alcohol and at least one water-swellable polymer, and said sugar alcohol and water-swellable polymers are present in a weight ratio of from about 2:1 to about 49:1.

In another embodiment, the present application relates to a method of treating Parkinson's disease in a patient in need thereof, which comprises administering to the patient a mouth-dissolving composition of rasagiline or a pharmaceutically-acceptable salt thereof, wherein said composition comprises less than or equal to about 1 mg of rasagiline or a pharmaceutically-acceptable salt thereof, at least one sugar alcohol and at least two water-swellable vinyl polymers.

In an aspect of the above embodiments, the mouth-dissolving composition of the present application comprises granules of rasagiline and one or more pharmaceutically-acceptable excipients.

In an aspect of the above embodiments, wherein said rasagiline granules has d(90) size of less than about 250 μm.

In another of the above embodiments, wherein said rasagiline granules has d(90) size in the range of about 100 μm to about 250 μm.

In an aspect of the above embodiments, wherein said rasagiline granules has d(50) size of less than about 75 μm.

In another of the above embodiments, wherein said rasagiline granules has d(50) size in the range of about 10 μm to about 75 μm.

In an aspect of the above embodiments, the mouth-dissolving composition of the present application may comprise porous granules, wherein such granules provide void or fine spaces in the composition, which normally allow saliva or water to infiltrate into the composition and accelerate release of the drug by improving the disintegration of composition across oral cavity. The porosity of granules of the present composition is at least about 30% when measured with respect to the ratio of void space to bulk volume.

The terms "porosity" and "porosity %", as used herein refers to void or fine spaces in the granules of the composition, which does not affect the inner or outer dimensions of said composition, the porosity as defined herein is expressed as, Porosity=(Bulk volume−True volume)/Bulk volume The mouth-dissolving composition should not be very hard and should be having sufficient breaking strength to allow easy administration. At the same time it should be convenient for handling/removal from the package without damaging the dose unit. The breaking strength of the present composition is about 10N to about 40N and the friability is less than 1.0%.

In an embodiment, the present application relates to a mouth-dissolving composition comprising granules of a therapeutically effective amount of rasagiline or a pharmaceutically-acceptable salt thereof and one or more pharmaceutically-acceptable excipients, wherein said composition has breaking strength of about 10N to about 40N.

In another embodiment, the present application relates to a mouth-dissolving composition comprising granules of a therapeutically effective amount of rasagiline or a pharmaceutically-acceptable salt thereof and one or more pharmaceutically-acceptable excipients, wherein said composition has friability of less than 1.0%.

The term, "bulk density" as used herein refers to the density of weighed quantity of the granules placed into graduated cylinder and measuring the volume and weight. Bulk density can be expressed as, Bulk density=Weight of the granules/Volume of the packing.

The term, "tapped density" as used herein refers to the density of weighed quantity of the granules placed into graduated cylinder and tapping the cylinder until no further change in volume is noted. Tapped density can be expressed as, Tapped Density=Weight of the granules/volume of the tapped packing In yet another aspect of the above embodiments, the mouth-dissolving composition of the present application comprising granules of rasagiline or a pharmaceutically-acceptable salt thereof, wherein said granules have a bulk density of less than about 0.5 gm/ml, and wherein said granules have a tapped density of less than about 0.7 gm/ml.

The mouth-dissolving composition of the present application optionally comprises at least one pH modifier selected from the group of acidic pH modifiers such as citric acid, tartaric acid, maleic acid, fumaric acid, succinic acid, maleic acid; alkalizers such as meglumine, sodium hydroxide, potassium hydroxide, sodium bicarbonate or buffering agents such as phosphate buffer, acetate buffer, borate buffer and the like or mixtures thereof. Such pH modifiers are present in an amount of from about 5% to about 7% by weight of the pharmaceutical composition.

The mouth-dissolving composition of the present application comprises at least one pH modifier selected from the group of acidic pH modifiers such as citric acid, tartaric acid, maleic acid, fumaric acid, succinic acid, maleic acid; alkalizers such as meglumine, sodium hydroxide, potassium hydroxide, sodium bicarbonate or buffering agents such as phosphate buffer, acetate buffer, borate buffer and the like or mixtures thereof. Such pH modifiers are present in an amount of from about 5% to about 7% by weight of the pharmaceutical composition.

The mouth-dissolving composition of the present application further comprises pharmaceutically-acceptable excipients selected from the group of diluents, lubricants, glidants, sweeteners, preservatives, antioxidants, solvent such as water and the like or mixtures thereof.

Suitable examples of diluents that may be used in the present application include, but are not limited to, cellulose derivatives such as methylcellulose, carboxymethylcellulose, microcrystalline cellulose and the like or mixtures thereof. Such diluents are present in an amount of from about 10% to about 20% by weight of the pharmaceutical composition.

Other suitable pharmaceutically-acceptable excipients that may be used to formulate the present mouth-dissolving composition, are any excipients known to a person skilled in the art, and are described in the Handbook of Pharmaceutical Excipients, American Pharmaceutical Association (1986), incorporated herein by reference.

In one embodiment, the mouth-dissolving composition of the present application is stable for at least about 3 months upon storage at 25° C./60% relative humidity (RH) or at 40° C./75% relative humidity (RH).

In an aspect of the above embodiments, the mouth-dissolving composition of the present application provides chemical and physical stability of the composition including N-propargylamine derivative such as rasagiline or a pharmaceutically-acceptable salt thereof, which does not change original shape, color, assay values and composition characteristics such as impurities, drug concentration, appearance and the like as disclosed herein, wherein the drug is present in an amount of at least about 95% to about 100% of the originally specified amount and total impurity of not more than about 1.5% for at least about 3 months upon storage at 25° C./60% relative humidity (RH) or at 40° C./75% relative humidity (RH).

In an embodiment, the mouth-dissolving composition of the present application comprising therapeutically effective amount of rasagiline or a pharmaceutically-acceptable salt thereof, at least one sugar alcohol and at least one water-swellable polymer, wherein said composition is stable for at least about 3 months upon storage at 25° C./60% relative humidity (RH) or at 40° C./75% relative humidity (RH).

In another embodiment, the mouth-dissolving composition of the present application comprising therapeutically effective amount of rasagiline or a pharmaceutically-acceptable salt thereof, at least one sugar alcohol and at least two water-swellable polymer, wherein said composition is stable for at least about 3 months upon storage at 25° C./60% relative humidity (RH) or at 40° C./75% relative humidity (RH).

In another embodiment, the mouth-dissolving composition of the present application comprising therapeutically effective amount of rasagiline or a pharmaceutically-acceptable salt thereof, at least one sugar alcohol and at least two water-swellable vinyl polymer, wherein said composition is stable for at least about 3 months upon storage at 25° C./60% relative humidity (RH) or at 40° C./75% relative humidity (RH).

In an aspect of the above embodiments, the mouth-dissolving composition of the present application can be packaged in any suitable packaging material known in the art that can ensure the stability of said composition and N-propargylamine derivative such as rasagiline or a pharmaceutically-acceptable salt thereof during storage, transit and administration.

In an aspect of the above embodiments, the mouth-dissolving composition of the present application can be packaged using suitable packaging materials selected from high-density polyethylene (HDPE) container, aluminum-aluminum (Alu-Alu) blister package or polyvinyl chloride—polyvinylidene chloride (PVC-PVdC) blister package and the like materials.

In an embodiment, the present application relates to a mouth-dissolving composition comprising a process to prepare granules of N-propargylamine derivative such as rasagiline or a pharmaceutically-acceptable salt thereof and one or more pharmaceutically-acceptable excipients, which includes any method known to a person skilled in the art such as, but not limited to, spraying a suspension or dispersion of drug in a conventional coating pan or fluidized bed equipment (such as a Wurster or Glatt) over sugar alcohol, alternatively granulating with sugar alcohol; followed by drying of the granules when desired granule size is achieved.

In an aspect of the above embodiments, the mouth-dissolving composition of the present application comprises a process to prepare granules, comprising the steps of: (a) preparing a mixture of therapeutically effective amount of N-propargylamine derivative or a pharmaceutically-acceptable salt thereof with required quantity of sugar alcohol and water-swellable vinyl polymers; (b) granulating required quantity of sugar alcohol and optionally pH modifier with the mixture of (a); (c) drying the granules of (b) and formulating into desired composition.

In an aspect of the above embodiments, the mouth-dissolving composition of the present application comprises a process to prepare granules, comprising the steps of: (a) preparing a mixture of therapeutically effective amount of rasagiline or a pharmaceutically-acceptable salt thereof with required quantity of at least one sugar alcohol and at least one water-swellable vinyl polymers; (b) granulating required quantity of sugar alcohol and optionally pH modifier with the mixture of (a); (c) drying the granules of (b) and formulating into desired composition.

In an aspect of the above embodiments, the mouth-dissolving composition of the present application comprises a process to prepare granules, comprising the steps of: (a) preparing a mixture of therapeutically effective amount of rasagiline or a pharmaceutically-acceptable salt thereof with required quantity of at least one sugar alcohol and at least two water-swellable vinyl polymers; (b) granulating required quantity of sugar alcohol and optionally pH modifier with the mixture of (a); (c) drying the granules of (b) and formulating into desired composition.

In an aspect of the above embodiments, the mouth-dissolving compositions of the present application can be formulated into solid dosage forms like, not limited to, sublingual tablets, orally disintegrating tablets, buccal tablets, oral tablets, lozenges, caplets, pills, powders, granules, sachets, films, and the like.

In an aspect of the above embodiments, the present application relates to a mouth-dissolving composition in the form of sublingual tablet comprising therapeutically effective amount of rasagiline or a pharmaceutically-acceptable salt thereof.

In another aspect of the above embodiments, the present application relates to a mouth-dissolving composition in the form of buccal tablet comprising therapeutically effective amount of rasagiline or a pharmaceutically-acceptable salt thereof.

In yet another aspect of the above embodiments, the present application relates to a mouth-dissolving composition in the form of orally disintegrating tablet comprising therapeutically effective amount of rasagiline or a pharmaceutically-acceptable salt thereof.

In an aspect of the above embodiments, the mouth-dissolving composition of the present application can be administered with or without food, along with a sip of liquid.

In another aspect of the above embodiments, the mouth-dissolving composition of the present application can be administered with or without food, and without a sip of liquid.

In yet another aspect of the above embodiments, the mouth-dissolving composition of the present application can be administered with or without food, and with a sip of liquid, wherein said liquid is selected from water or food dispersions like sauce, puree, jam or food syrups.

In yet another aspect of the above embodiments, the present mouth-dissolving composition comprising N-propargylamine derivative such as rasagiline can also be co-administered (simultaneously or sequentially) with one or more pharmaceutical agents of value in treating Parkinson's disease or related disease conditions.

The present application is further illustrated by the examples which are provided merely to be exemplary of the pharmaceutical composition described above and do not limit the scope of the application. Certain modifications and equivalents will be apparent to those skilled in the art and are intended to be included within the scope of the present application.

EXAMPLES

Examples 1-2

The mouth-dissolving composition comprising therapeutically effective amount of rasagiline or a pharmaceutically-acceptable salt thereof may be prepared as given in table 1.

TABLE 1

| Composition | Example - 1 (% w/w) | Example - 2 (% w/w) | Example - 3 (% w/w) | Example - 4 (% w/w) |
|---|---|---|---|---|
| Mannitol | 92.56 | 69.88 | 91.26 | 91 |
| Citric acid | — | 6.55 | — | — |
| Rasagiline Mesylate | 0.83 | 1.38 | 0.8 | 0.8 |
| Polyvinyl Alcohol | 0.4 | 0.33 | 0.4 | 0.4 |
| Acesulfam Potassium | 0.2 | 0.16 | 0.2 | 0.2 |
| Crospovidone | 4.0 | 3.3 | 5.34 | 5.6 |
| Microcrystalline Cellulose | — | 16.66 | — | — |
| Stearic acid | 2.0 | 1.66 | 2.0 | 2.0 |
| Total | 100 | 100 | 100 | 100 |

Procedure:

1. Mannitol in an amount of about 55% to about 80%, stearic acid, citric acid anhydrous or microcrystalline cellulose were sifted as required through specified mesh.
2. Rasagiline mesylate, mannitol in an amount of about 15%, polyvinyl alcohol, acesulfam potassium and crospovidone were dissolved in purified water and mixed for 10 minutes.
3. Mannitol in an amount of about 55% to about 80% or mannitol in an amount of about 55% to about 80% and citric acid as required were granulated with the mixture of step (2) and dried to get desired limit of loss on drying (LOD).
4. Granules as prepared in step (3) were sifted through specified mesh and blended with microcrystalline cellulose as required for a specified time using blender, followed by lubricating with stearic acid for specified time.
5. Blended granules as prepared in step (4) were compressed as per the specified parameters to make tablets and packed into suitable packs.

Example 5

The mouth-dissolving compositions as prepared in example 1-4 were subjected to dissolution studies at 20 rpm in 5 ml of pH 6.75 simulated saliva at 37° C. and the results are given in table 2.

TABLE 2

| Time (minutes) | Example - 1 | Example - 2 | Example - 3 | Example - 4 |
|---|---|---|---|---|
| | | % Drug dissolved | | |
| 0 | 0 | 0 | 0 | 0 |
| 2 | 80 | 85 | 72 | 74 |
| 5 | 82 | 86 | 88 | 82 |
| 10 | 90 | 88 | 95 | 82 |

Example 6

The mouth-dissolving compositions as prepared in example 1-4 were subjected to disintegration studies using USP Disintegration Test Apparatus with purified water at 37° C. and the results are given in table 3.

TABLE 3

| Examples | Time (Seconds) |
|---|---|
| 1 | 10-14 |
| 2 | 10-14 |
| 3 | 16-19 |
| 4 | 11-12 |

Example 7

The pharmacokinetic parameters for mouth-dissolving compositions as prepared in example 1-4 were studied in comparison with AZILECT® (1 mg) oral tablets by using a single dose, three-way, randomized crossover method as mentioned below.

Example 1-2

The pharmacokinetic study was conducted in total 18 healthy human subjects in fasting condition and the subjects were administered a single dose of composition of examples 1-2 by sublingual route. The results are shown in below Table 4 and the mean plasma rasagiline concentration vs. time profile vis-a-vis AZILECT® is shown in FIG. 1.

TABLE 4

| Parameters | Example 1 | Example 2 | AZILECT® (1 mg) |
|---|---|---|---|
| $C_{max}$ (pg/ml) | 4031 | 5356 | 5401 |
| $T_{lag}$ (min) | 0 | 5 | 10 |
| $T_{max}$ (min) | 15 | 15 | 25.2 |
| $AUC_{(0-10\ min)}$ (pg · hr/ml) | 184 | 152 | 59 |
| $AUC_{(0-25\ min)}$ (pg · hr/ml) | 1022 | 1187 | 860 |
| $AUC_{(0-t)}$ (pg · hr/ml) | 2613 | 3758 | 3390 |
| $AUC_{(0-\infty)}$ (pg · hr/ml) | 2526 | 3610 | 3361 |
| $AUC_{(0-refTmax)}$ (pg · hr/ml) | 902 | 1046 | 658 |

Example 3

Figure 2:
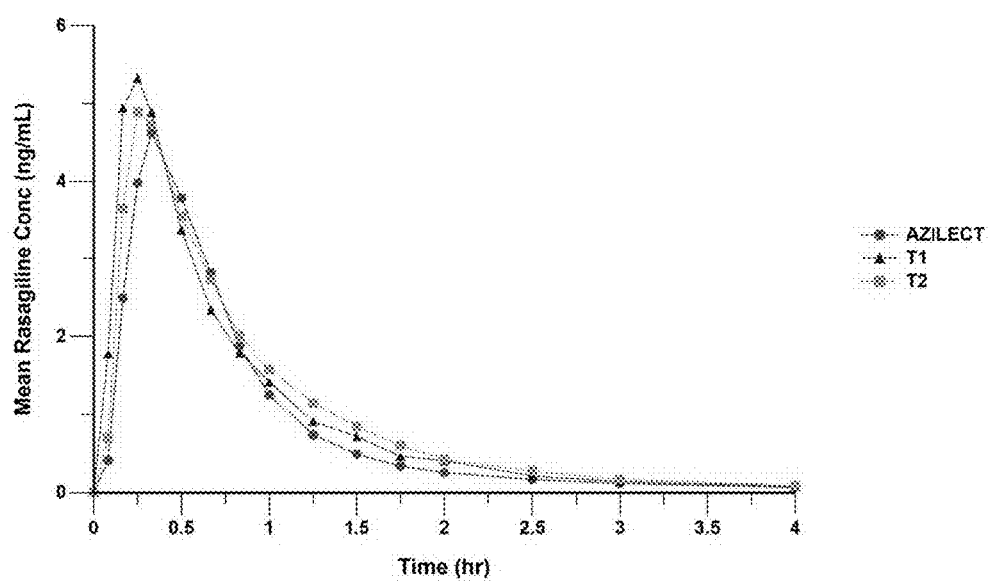
FIG. 2 shows 4-hour plasma rasagiline concentration vs. time profile for an exemplary composition of the present application, as set forth in Example 3, vis-à-vis 1 mg of AZILECT® administered by sublingual (T1) and buccal (T2) routes to 15 healthy human subjects in fasting conditions.

The pharmacokinetic study was conducted in total 15 healthy human subjects in fasting condition and the subjects were administered a single dose of composition of example 3 by sublingual (T1) and buccal (T2) routes. The results are shown in below Table 5 and the mean plasma rasagiline concentration vs. time profile vis-a-vis AZILECT® is shown in FIG. 2.

TABLE 5

| | Example 3 | | AZILECT® |
|---|---|---|---|
| Parameters | T1 | T2 | (1 mg) |
| $C_{max}$ (pg/ml) | 5770 | 5570 | 5340 |
| $T_{lag}$ (min) | 5 | 5 | 10 |
| $T_{max}$ (min) | 15 | 19.8 | 19.8 |
| $AUC_{(0-5\ min)}$ (pg · hr/ml) | 70 | 30 | 20 |
| $AUC_{(0-10\ min)}$ (pg · hr/ml) | 360 | 210 | 140 |
| $AUC_{(0-20\ min)}$ (pg · hr/ml) | 1190 | 950 | 750 |
| $AUC_{(0-t)}$ (pg · hr/ml) | 4220 | 4360 | 3650 |
| $AUC_{(0-\infty)}$ (pg · hr/ml) | 4300 | 4430 | 3710 |
| $AUC_{(0-refTmax)}$ | 1190 | 950 | 750 |
| $T_{lag}$ (min) | | | |

Example 4

Figure 3:
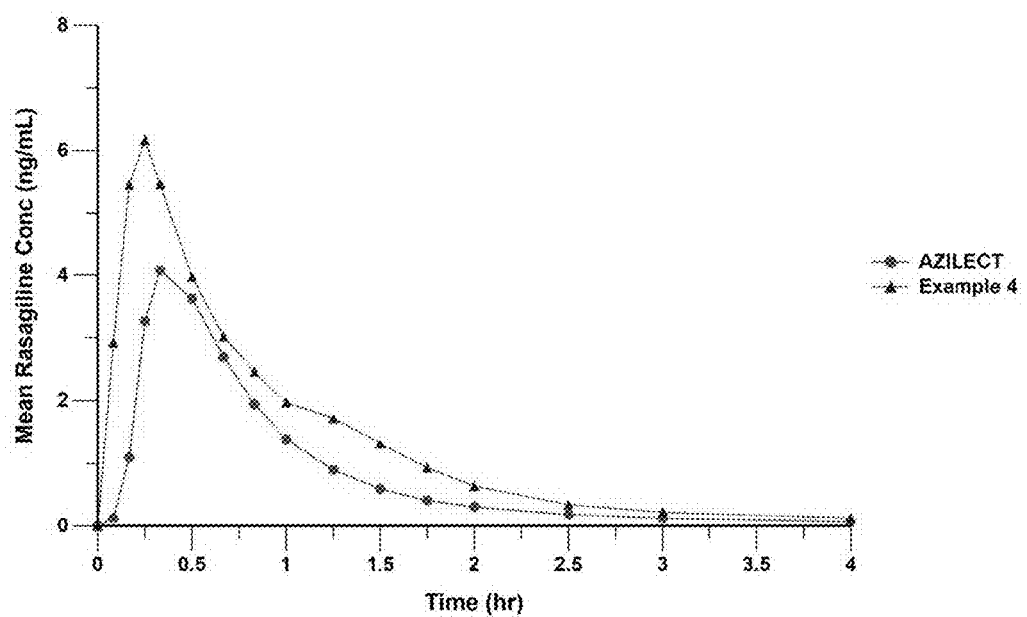
FIG. 3 shows 4-hour plasma rasagiline concentration vs. time profile for an exemplary composition of the present application, as set forth in Example 4, vis-à-vis 1 mg of AZILECT® administered as orally disintegrating tablets to 16 healthy human subjects in fasting conditions.

The pharmacokinetic study was conducted in total 16 healthy human subjects in fasting condition and the subjects were administered a single dose of composition of example 4 as orally disintegrating tablets. The results are shown in below Table 6 and the mean plasma rasagiline concentration vs. time profile vis-a-vis AZILECT® is shown in FIG. 3.

TABLE 6

| Parameters | Example 4 | AZILECT® (1 mg) |
|---|---|---|
| $C_{max}$ (pg/ml) | 6873 | 4820 |
| $T_{lag}$ (min) | 0 | 5 |
| $T_{max}$ (min) | 15 | 19.8 |
| $AUC_{(0-5\ min)}$ (pg · hr/ml) | 114 | 5 |
| $AUC_{(0-10\ min)}$ (pg · hr/ml) | 443 | 59 |
| $AUC_{(0-20\ min)}$ (pg · hr/ml) | 1333 | 533 |
| $AUC_{(0-t)}$ (pg · hr/ml) | 5480 | 3420 |
| $AUC_{(0-\infty)}$ (pg · hr/ml) | 5560 | 3500 |

Example 8

The mouth-dissolving compositions as prepared in example 3-4 were studied for physical and chemical stability at 25° C./65 RH and at 40° C./75 RH for 3 months using various packaging materials selected from high-density polyethylene (HDPE) container, aluminum-aluminum (Alu-Alu) blister package or polyvinyl chloride—polyvinylidene chloride (PVC-PVdC) blister package or and the results are shown in below Tables 7, 8 and 9 respectively.

TABLE 7

(High-density polyethylene (HDPE) container)

| | Example 3 | | | Example 4 | | |
|---|---|---|---|---|---|---|
| | | 3 months | | | 3 months | |
| Parameters | Initial | 25° C./60% RH | 40° C./75% RH | Initial | 25° C./60% RH | 40° C./75% RH |
| Description | White colored round tablet plain on both sides | White colored round tablet plain on both sides | White colored round tablet plain on both sides | White colored round tablet plain on both sides | White colored round tablet plain on both sides | White colored round tablet plain on both sides |
| Assay (% w/v) | 101.3 | 101.3 | 99.0 | 98.7 | 98.7 | 97.9 |
| Related Substances (%) | | | | | | |
| RAS-1 Impurity | 0.02 | 0.05 | 0.15 | 0.03 | 0.16 | 0.14 |
| Any individual maximum impurity | 0.13 | 0.13 | 0.19 | 0.12 | 0.15 | 0.14 |
| Total impurity | 0.27 | 0.34 | 0.53 | 0.19 | 0.49 | 0.51 |
| Dissolution at USP II/pH 6.5 Phosphate Buffer/500 ml/50 rpm | | | | | | |
| Time | Initial | 3 months | | Initial | 3 months | |
| 15 minutes | 101 | 100 | 99 | 101 | 100 | 100 |

TABLE 8

(Aluminum-Aluminum (Alu-Alu) blister package)

| | Example 3 | | | Example 4 | | |
|---|---|---|---|---|---|---|
| | | 3 months | | | 3 months | |
| Parameters | Initial | 25° C./60% RH | 40° C./75% RH | Initial | 25° C./60% RH | 40° C./75% RH |
| Description | White colored round tablet plain on both sides | White colored round tablet plain on both sides | White colored round tablet plain on both sides | White colored round tablet plain on both sides | White colored round tablet plain on both sides | White colored round tablet plain on both sides |
| Assay (% w/v) | 101.3 | 101.1 | 99.7 | 98.7 | 99.9 | 99.9 |
| Related Substances (%) | | | | | | |
| RAS-1 Impurity | 0.02 | 0.14 | 0.24 | 0.03 | 0.06 | 0.16 |
| Any individual maximum impurity | 0.13 | 0.15 | 0.17 | 0.12 | 0.09 | 0.11 |
| Total impurity | 0.27 | 0.56 | 0.83 | 0.19 | 0.26 | 0.46 |
| Dissolution at USP II/pH 6.5 Phosphate Buffer/500 ml/50 rpm | | | | | | |
| Time | Initial | 3 months | | Initial | 3 months | |
| 15 minutes | 101 | 97 | 93 | 101 | 92 | 98 |

TABLE 9

(Polyvinyl chloride-Polyvinylidene chloride (PVC-PVdC) blister package)

| | Example 3 | | | Example 4 | | |
|---|---|---|---|---|---|---|
| | | 3 months | | | 3 months | |
| Parameters | Initial | 25° C./60% RH | 40° C./75% RH | Initial | 25° C./60% RH | 40° C./75% RH |
| Description | White colored round tablet plain on both sides | White colored round tablet plain on both sides | White colored round tablet plain on both sides | White colored round tablet plain on both sides | White colored round tablet plain on both sides | White colored round tablet plain on both sides |
| Assay (% w/v) | 101.3 | 99.9 | 99.5 | 98.7 | 100.2 | 99.4 |
| Related Substances (%) | | | | | | |
| RAS-1 Impurity | 0.02 | 0.10 | 0.14 | 0.03 | 0.07 | 0.29 |
| Any individual maximum impurity | 0.13 | 0.12 | 0.15 | 0.12 | 0.09 | 0.35 |
| Total impurity | 0.27 | 0.49 | 0.56 | 0.19 | 0.30 | 1.15 |

| Dissolution at USP II/pH 6.5 Phosphate Buffer/500 ml/50 rpm | | | | |
|---|---|---|---|---|
| Time | Initial | 3 months | Initial | 3 months |
| 15 minutes | 101 | 99 | 99 | 101 | 100 | 96 |

While several particular forms of the application have been illustrated and described, it will be apparent that various modifications and combinations of the application detailed in the text can be made without departing from the spirit and scope of the application.

We claim:

1. A mouth dissolving composition of rasagiline or a pharmaceutically-acceptable salt thereof, comprising:
   (a) rasagiline in an amount less than or equal to 1 mg;
   (b) at least one sugar alcohol in an amount of 50% to 80% by weight of the composition;
   (c) at least two polymers of N-vinylpyrrolidone selected from the group consisting of crospovidone and copovidone, polyvinyl alcohol, polyvinyl acetate, copolymers thereof, and mixtures thereof, wherein the total amount of said polymers is present in an amount from about 0.2% to about 5.0% by weight of the composition; and
   (d) one or more pharmaceutically-acceptable excipients.

2. The composition of claim 1, wherein said sugar alcohol and said polymers are present in a weight ratio of from about 2:1 to about 49:1.

3. The composition of claim 1, wherein said sugar alcohol is selected from the group consisting of mannitol, sorbitol, xylitol, erythritol, threitol, and mixtures thereof.

4. The composition of claim 1, wherein said composition comprises at least one pH modifier.

5. The composition of claim 4, wherein said pH modifier is selected from the group consisting of citric acid, tartaric acid, maleic acid, fumaric acid, succinic acid, maleic acid, meglumine, sodium hydroxide, potassium hydroxide, sodium bicarbonate, and mixtures thereof.

6. The composition of claim 1, wherein said composition is stable for at least about 3 months upon storage at 25° C./60% relative humidity (RH), or at 40° C./75% relative humidity (RH).

7. The composition of claim 1, wherein said mouth dissolving composition is selected from the group consisting of sublingual tablets, rapidly disintegrating tablets, buccal tablets, lozenges, caplets, pills, wafers, films, powders, granules, and sachets.

8. The composition of claim 1, wherein when said composition is placed inside oral cavity of a patient, said composition dissolves or disintegrates in less than about 60 seconds in the oral cavity.

9. A method of treating Parkinson's disease in a patient in need thereof comprising administering to the patient a mouth dissolving composition of rasagiline or a pharmaceutically-acceptable salt thereof, wherein said composition comprises:
   (a) rasagiline in an amount less than or equal to 1 mg;
   (b) at least one sugar alcohol in an amount of 50% to 80% by weight of the composition;
   (c) at least two polymers of N-vinylpyrrolidone selected from the group consisting of crospovidone and copovidone, polyvinyl alcohol, polyvinyl acetate, copolymers thereof, and mixtures thereof, wherein the total amount of said polymers is present in an amount from about 0.2% to about 5.0% by weight of the composition; and
   (d) one or more pharmaceutically-acceptable excipients.

10. The method of claim 1, wherein administering said composition comprises placing said composition inside the oral cavity.

11. The method of claim 10, wherein said composition dissolves or disintegrates in less than about 60 seconds.

12. The method of claim 1, wherein said sugar alcohol and said polymers are present in a weight ratio of from about 2:1 to about 49:1.

13. The method of claim 9, wherein upon administration said composition releases at least about 70% of said rasagiline within about 2 minutes when measured in 5 ml of pH 6.75 simulated saliva at 20 rpm and at 37° C.

14. The method of claim 9, wherein said composition comprises a sugar alcohol selected from the group consisting of mannitol, sorbitol, xylitol, erythritol, threitol, and mixtures thereof.

15. The method of claim 9, wherein said composition comprises at least one pH modifier.

16. The method of claim 15, wherein said pH modifier is selected from the group consisting of citric acid, tartaric acid, maleic acid, fumaric acid, succinic acid, maleic acid, meglumine, sodium hydroxide, potassium hydroxide, sodium bicarbonate, and mixtures thereof.

17. The method of claim 9, wherein said composition is stable for at least about 3 months upon storage at 25° C./60% relative humidity (RH), or at 40° C./75% relative humidity (RH).

18. The method of claim 9, wherein said mouth dissolving composition is selected from the group consisting of sublingual tablets, rapidly disintegrating tablets, buccal tablets, lozenges, caplets, pills, wafers, films, powders, granules, and sachets.

* * * * *